US007727221B2

(12) United States Patent
Penner et al.

(10) Patent No.: US 7,727,221 B2
(45) Date of Patent: Jun. 1, 2010

(54) METHOD AND DEVICE FOR ELECTROCHEMICAL FORMATION OF THERAPEUTIC SPECIES IN VIVO

(75) Inventors: Avi Penner, Tel Aviv (IL); Eilezer Gileadi, Herzliya Pituach (IL)

(73) Assignee: Cardiac Pacemakers Inc., Saint Paul, MN (US)

( * ) Notice: Subject to any disclaimer, the term of this patent is extended or adjusted under 35 U.S.C. 154(b) by 328 days.

(21) Appl. No.: 10/477,514

(22) PCT Filed: Jun. 27, 2002

(86) PCT No.: PCT/IL02/00524

§ 371 (c)(1),
(2), (4) Date: Nov. 19, 2003

(87) PCT Pub. No.: WO03/002243

PCT Pub. Date: Jan. 9, 2003

(65) Prior Publication Data

US 2004/0230225 A1   Nov. 18, 2004

(51) Int. Cl.
*A61M 31/00* (2006.01)
*A61F 2/06* (2006.01)

(52) U.S. Cl. .................... 604/500; 623/1.46
(58) Field of Classification Search ............... 604/20; 607/2, 75, 50; 623/1.1–1.54
See application file for complete search history.

(56) References Cited

U.S. PATENT DOCUMENTS

| | | | |
|---|---|---|---|
| 3,868,578 A | | 2/1975 | Oldham |
| 5,360,440 A | * | 11/1994 | Andersen ................... 607/115 |
| 5,458,627 A | | 10/1995 | Baranowski, Jr. et al. |
| 5,797,898 A | | 8/1998 | Santini, Jr. et al. |
| 5,833,715 A | | 11/1998 | Vachon et al. |
| 5,843,089 A | * | 12/1998 | Sahatjian et al. ........... 623/1.11 |
| 5,873,904 A | * | 2/1999 | Ragheb et al. ............. 623/1.13 |
| 5,880,661 A | | 3/1999 | Davidson et al. |
| 5,938,903 A | | 8/1999 | Broderick |
| 5,951,458 A | | 9/1999 | Hastings et al. |
| 5,976,169 A | * | 11/1999 | Imran ....................... 623/1.15 |
| 5,980,554 A | * | 11/1999 | Lenker et al. .............. 606/198 |
| 6,021,347 A | | 2/2000 | Herbst et al. |
| 6,080,190 A | * | 6/2000 | Schwartz ................... 623/1.22 |
| 6,123,861 A | | 9/2000 | Santini, Jr. et al. |
| 6,140,740 A | | 10/2000 | Porat et al. |
| 6,162,238 A | | 12/2000 | Kaplan et al. |
| 6,164,284 A | | 12/2000 | Schulman et al. |
| 6,167,307 A | | 12/2000 | Hess |
| 6,170,488 B1 | | 1/2001 | Spillman, Jr. et al. |
| 6,185,455 B1 | | 2/2001 | Loeb et al. |
| 6,185,457 B1 | | 2/2001 | Kroll et al. |

(Continued)

OTHER PUBLICATIONS

Chou et al., "Electrochemical treatment of mouse and rat fibrosarcomas with direct current," *Bioelectromagnetics*, 1997, 18:14-24.

(Continued)

*Primary Examiner*—Mark W Bockelman
(74) *Attorney, Agent, or Firm*—Fish & Richardson P.C.

(57) ABSTRACT

A device and method are provided for spontaneous electrochemical production of therapeutic species, in vivo. An active metal is implanted in the tissue. The metal undergoes corrosion, thus acting as a reducing agent to constituents in the tissue, so as to cause these constituents to form the therapeutic agents.

83 Claims, 8 Drawing Sheets

U.S. PATENT DOCUMENTS

| | | | |
|---|---|---|---|
| 6,201,991 B1 | 3/2001 | Chekanov | |
| 6,206,914 B1 * | 3/2001 | Soykan et al. | 623/1.42 |
| 6,277,078 B1 | 8/2001 | Porat et al. | |
| 6,287,332 B1 * | 9/2001 | Bolz et al. | 623/1.15 |
| 6,366,808 B1 | 4/2002 | Schroeppel et al. | |
| 6,486,588 B2 | 11/2002 | Doron | |
| 6,584,349 B1 * | 6/2003 | Sage et al. | 604/20 |
| 6,585,764 B2 * | 7/2003 | Wright et al. | 623/1.42 |
| 6,628,989 B1 | 9/2003 | Penner | |
| 6,660,034 B1 * | 12/2003 | Mandrusov et al. | 623/1.42 |

OTHER PUBLICATIONS

Li et al., "Effects of Direct Current on Dog Liver: Possible Mechanisms for Tumor Electrochemical Treatment," *Bioelectromagnetics*, 1997, 18:2-7.

*Methods in Cell Biology (Cell Death)*, vol. 46, p. 163.

James A. Plambeck, "Electrolytic Processes of Nonmetals," *Chemical Sciences*, 1995, 2 pages.

Ren et al., "Variations of dose and electrode spacing for rat breast cancer electrochemical treatment," *Bioelectromagnetics*, 2001, 22(3):205-211.

Stoner et al., "The mechanism of low frequency a.c. Electrochemical Disinfection," *Bioelectrochemistry and Bioenergetics*, 1982, 9:229-243.

Turler et al., "Experimental low-level direct current therapy in liver metastases: influence of polarity and current dose," *Bioelectromagnetics*, 2000, 21(5):395-401.

Xin et al., "Electrochemical Treatment of Lung Cancer," *Bioelectromagnetics*, 1997, 18:8-13.

Yen et al., "Electrochemical treatment of human KB cells in vitro," *Bioelectromagnetics*, 1999, 20:34-41.

* cited by examiner

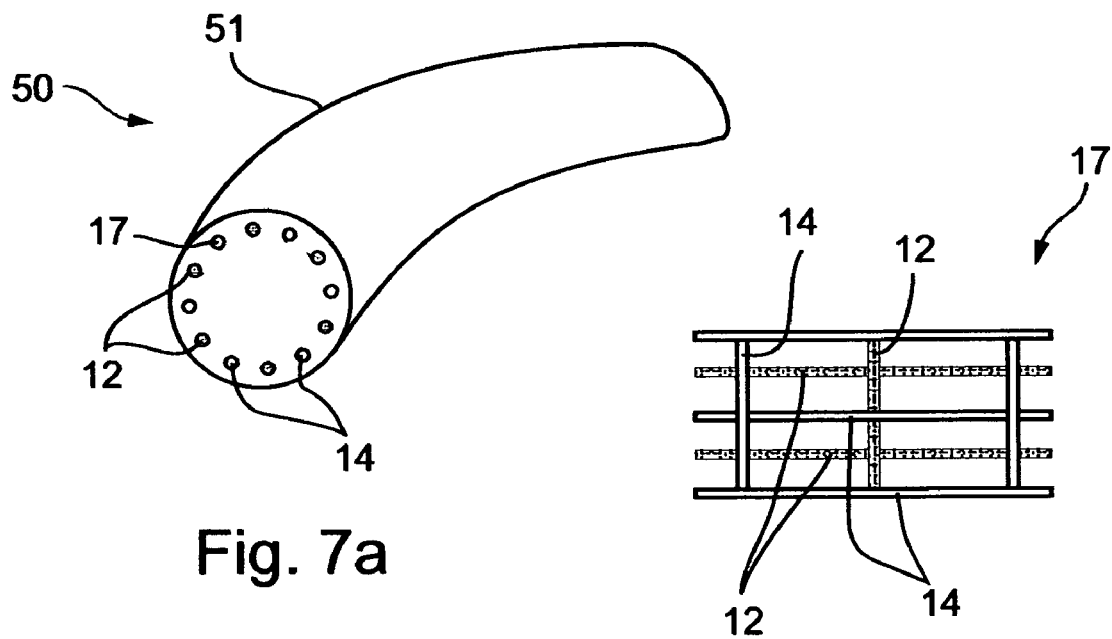
Fig. 7a
Fig. 7b
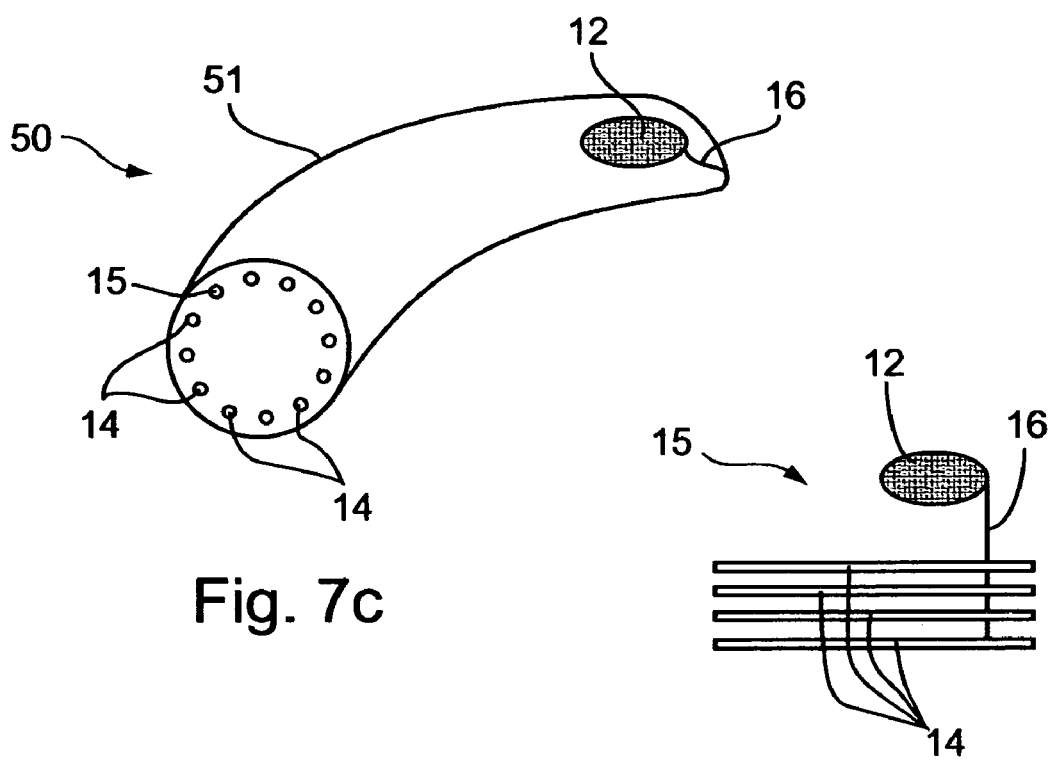
Fig. 7c
Fig. 7d

METHOD AND DEVICE FOR ELECTROCHEMICAL FORMATION OF THERAPEUTIC SPECIES IN VIVO

FIELD OF THE INVENTION

The present invention relates generally to in vivo electrochemical formation of therapeutic species, and in particular, to in vivo electrochemical formation of therapeutic species with no use of external power.

BACKGROUND OF THE INVENTION

Electrochemical reactions are chemical reactions in which electrons are transferred from one atom to another. Electrochemistry is thus a branch of chemistry that deals with the chemical changes produced by electricity and conversely, the production of electricity by chemical changes. A basic overview of electrochemistry may be obtained, for example, from Stoner et al. Bioelectrochemistry and Bioengineering, 9, (1982) 229-243.

Three types of electrochemical reactions may be distinguished, as follows:

i. An oxidation reaction, in which electrons are lost by atoms of the species involved in the reaction, so that the atoms become more positive, i.e., their oxidation state increases. In an oxidation reaction, electrons appear as products.

ii. A reduction reaction, in which electrons are gained by the species involved in the reaction, so that they become less positive, i.e., their oxidation state decreases. In a reduction reaction, electrons appear as reactants.

iii. A redox reaction, which involves both a reduction and an oxidation, and is called redox as an abbreviation to these. The stoichiometry of a redox reaction is such that all the electrons lost in the oxidation are gained in the reduction, so in a redox reaction, electrons do not appear explicitly.

One may thus define a reducing agent, as a species that reduces another species, and is itself oxidized in the process. Similarly, one may define an oxidizing agent, as a species that oxidizes another species, and is itself reduced in the process.

Two types of electrical conductors are operative in electrochemical reactions. An electronic conductor, such as a metal, and an ionic conductor, such as a solution containing ions, often called an electrolyte solution, or an electrolyte.

An electronic conductor, such as a metal, in contact with an electrolyte, is termed, an electrode. An electrode on whose surface an oxidation reaction takes place is defined as an anode. The anode acts as an electron sink to the electrolyte. Similarly, an electrode on whose surface a reduction reaction takes place is a cathode. The cathode acts as an electron source to the electrolyte.

In corrosion reactions, an electrochemical reaction may be sustained by a single metal, immersed in an electrolyte. The corroding metal acts both as the anode and the cathode. For example, when a strip of zinc is immersed in an acidic solution, an oxidation reaction takes place on its surface, as follows:

$$Zn \rightarrow Zn^{2+} + 2e^- \quad [I]$$

This process cannot continue for any significant length of time, without a suitable cathodic process, in which the electrons are consumed. Thus the strip of metal zinc also acts as a cathode, providing a nucleation site and a source for the electrons, for example, in the cathodic reaction:

$$2H^+ + 2e^- \rightarrow H_2 \quad [II]$$

Corrosion reactions may also take place in a neutral environment, wherein the cathodic reaction may cause the solution to become more alkaline:

$$O_2 + 2H_2O + 4e^- \rightarrow 4(OH)^- \quad [III]$$

Although the zinc strip may act both as anode and as cathode, the addition of a second conducting strip, connected by wire to the zinc strip, will form an electrode pair. If the second strip is less active than the zinc, then the zinc strip will operate as the anode, and the second strip will operate as the cathode.

Certain metals such as platinum, though inert to electrochemical reactions, have a catalytic effect on the corrosion reaction. For example, when using platinum as a cathode, for reaction [II], the rate of the reaction may increase by a factor of $10^4$-$10^5$, compared to its rate on zinc Two or more electrodes, immersed in an electrolyte and connected by an electronic conductor, form an electrochemical cell.

In a galvanic electrochemical cell, current flows, power is produced, and the cell reaction proceeds spontaneously.

In an electrolytic electrochemical cell, current flows, power is consumed, and the cell reaction, which is driven, is the reverse of the spontaneous reaction of the glavanic cell.

In a reversible electrochemical cell, an infinitesimal change in cell potential can cause the reaction to proceed in either direction.

Chemists have selected the electrode reaction of hydrogen, under standard conditions of pressure and concentration, as a basis against which others electrode reactions are compared, and have termed it, standard hydrogen electrode (S.H.E.). The physically measured potential difference across a reversible cell made up of any electrode and a standard hydrogen electrode is called the reversible potential of the electrode, E. If the electrode (other than hydrogen) is also being operated under standard conditions of pressure and concentrations, the potential difference across the cell is the standard electrode potential, $E^0$ of the electrode other than hydrogen.

The Nernst Equation for an electrode links the actual (measurable) reversible potential of an electrode E, to the standard reversible potential, $E^0$. It may be described as:

$$E = E^0 - (0.05915/n)\log(\text{activity of the reactants/activity of the products}),$$

where n is the reaction charge (the number of electrons that are transferred).

Another use of the Nernst equation is to provide the activity ratio, which is approximately equal to the concentration ratio between the reactants and products. Given the reversible potential at an electrode E, and the concentration of the reactants, the concentration of the products may be calculated, and vise versa.

While electrochemistry is extensively applied in many technological fields, its application in vivo is limited to fewer reports and applications.

Electrochemical treatment of tumors is referred to in the medical literature as ECT.

In an ECT procedure, electrodes are implanted at spaced positions in or around the malignant tumor to be treated. Applied across these electrodes is a low DC voltage usually having a magnitude of less than 10 volts, causing a current to flow between the electrodes through the tumor. Due to an electrochemical process, reaction products are formed, which include cytotoxic agents that act to destroy the tumor cells.

In the ECT technique disclosed by Li et al., in Bioelectromagnetic 18:2-7 (1997), in the article "Effects of Direct Current on Dog Liver: Possible Mechanisms For Tumor Electrochemical Treatment" two platinum anode and cathode electrodes were inserted in a dog's liver with a 3 cm separation therebetween. Applied across these electrodes was a DC voltage of 8.5 volts, giving rise to an average current through the liver of 30 mA. This was continued for 69 minutes, with a total charge of 124 coulombs.

The concentration of selected ions near the anode and cathode were measured. The concentration of $Na^+$ and $K^+$ ions were found to be higher around the cathode, whereas the concentration of $Cl^-$ ions was higher around the anode. Water content and pH were determined near the anode and cathode, the pH values being 2.1 near the anode and 12.9 near the cathode. The released gases were identified as chlorine at the anode and hydrogen at the cathode. The series of electrochemical reactions which took place during ECT resulted in the rapid and complete destruction of both normal and tumor cells in the liver.

Another example of ECT appears in the article "Electrochemical Treatment of Lung Cancer" by Xin et al. in Bioelectromagnetics 18:8-13 (1997). In this ECT procedure platinum electrodes were inserted transcutaneously into a tumor, the voltage applied thereto was in the 6-8 volt range, the current was in the 40 to 100 mA range, and the electric charge, 100 coulombs per cm of tumor diameter.

According to this article, the clinical results indicate that ECT provides a simple, safe and effective way of treating lung cancers that are surgically inoperable and are not responsive to chemotherapy or radiotherapy.

Also disclosing ECT techniques are Chou et al., Bioelectromagnetics 18:14-24 (1997); Yen et al., Bioelectromagnetics 20:34-41 (1999); Turler at al., Bioelectromagnetics 21:395-401 (2000); Ren at al., Bioelectromagnetics 22:205-211 (2001); U.S. Pat. No. 5,360,440 to Andersen and U.S. Pat. No. 6,021,347 to Herbst et al.

Electrochemical reactions as a function of pH and electrode potential can be predicted by means of a Pourbaix diagram, as disclosed in the Atlas of Electrochemical Equilibria in Aqueous Solutions—Pergamon Press, 1986—by Pourbaix.

While U.S. Pat. No. 5,458,627 to Baranowski Jr., et al. does not relate to ECT but to the electrochemically controlled stimulation of osteogenesis, it is nevertheless of prior art interest, for it discloses that reaction products produced by an electrochemical reaction includes not only hydrogen and oxygen, but also hydrogen peroxide.

In the text Methods in Cell Biology, Vol. 46—Cell Death—published by Academic Press, it is noted (on page 163), that hydrogen peroxide has been reported to be an inducer of cell death in various cell systems. This type of cell death is attributed to the direct cytotoxicity of $H_2O_2$ and other oxidant species generated from $H_2O_2$.

The above described ECT technologies are limited in several aspects. First, they all pertain to the treatment of solid tumor masses, yet other applications are not envisaged. Second, they all fail to teach implantable electrochemical devices which are controlled and/or powered via telemetry.

U.S. Pat. Nos. 5,797,898 and 6,123,861 to Santini Jr. et al. both describe microchips which comprise a plurality of drug containing capped reservoirs, whereas in one embodiment the release of the drug therefrom is effected by disintegration of the caps via an electrochemical reaction.

While Santini Jr. et al. teach an electrochemical in vivo drug release mechanism effected by telemetry, Santini Jr. et al. fails to teach the in vivo electrochemical production of therapeutic agents.

U.S. Pat. No. 6,185,455, teaches functional neuromuscular stimulation (FNS) or functional electrical stimulation (FES) devices, designed also to locally release drugs that inhibit physiological reactions against the devices.

U.S. Pat. No. 5,938,903 teaches a microelectrode for inserting in vivo, in vitro into a warm-blooded or cold blooded animal brain or body, or extra-corporeally and measuring intracellular and/or extracellular concentration and/or release and/or reuptake of one or more biogenic chemicals while measuring said chemical in vivo or in vitro.

U.S. Pat. No. 5,833,715 teaches a pacing lead having a stylet introduced anti-inflammatory drug delivery element advanceable from the distal tip electrode. The element is formed as a moldable biocompatible composite material. The element has a biocompatible matrix material which may be combined with drugs and therapeutic agents to deliver the drugs and agents by co-dissolution or diffusion to the point of either passive or active fixation. The drug delivery element may be rigid and serve to center an active fixation mechanism, preferably a helix, which penetrates the myocardium.

U.S. Pat. No. 3,868,578 teaches a method and apparatus for electroanalysis.

U.S. Pat. No. 6,201,991 teaches a method and system for preventing or treating atherosclerosis in which a blood vessel susceptible to or containing atherosclerotic plaque is subjected to a low-frequency electrical impulse at an effective rate and amplitude to prevent or impede the establishment or decrease the size of the plaque in the vessel. The system can be implanted into the body of a patient or applied externally to the skin.

U.S. Pat. No. 5,360,440 teaches an apparatus for the in situ generation of an electrical current in a biological environment characterized by including an electrolytic fluid. The apparatus comprises first and second electrodes of differing electrochemical potentials separated by an insulator. The apparatus is adapted to be implanted in the environment. The presence of the electrolytic fluid and formation of a current path by hyperplastic cells bridging the electrodes enables electrolysis to occur and a direct current to pass through the current path to impede hyperplastic cell growth.

U.S. Pat. No. 6,206,914 teaches an implantable system that includes a carrier and eukaryotic cells, which produce and release a therapeutic agent, and a stimulating element for stimulating the release of the therapeutic agent. The system can also include a sensing element for monitoring a physiological condition and triggering the stimulating element to stimulate the delivery device to release the therapeutic agent. Alternatively, the patient in whom the system is implanted can activate the stimulating element to release the therapeutic agent. In one embodiment the carrier is medical electrical electrodes.

U.S. Pat. No. 6,366,808 describes an implantable electrical method and apparatus for the treatment of cancer tumors based on the usage of various levels of electrical fields and current to assist in specific ways to reduce tumor size. The method comprises: (1) implanting at least one electrode into or near a tumor, (2) implanting a source of electrical power, (3) connecting the electrode to the source of electrical power and (4) delivering electrical current into the tumor. Alternatively, the method comprises: (1) implanting at least one electrode into a tumor, (2) implanting a source of electrical power, (3) connecting the electrode to the source of electrical power, (4) monitoring at least one voltage from within tissue, and (5) delivering electrical current into the tumor. In both cases, it is the electrical current that provides the therapeutic action.

U.S. Pat. No. 5,951,458 describes a method for inhibiting restenosis by local application of an oxidizing agent to blood vessel walls. Preferred oxidizing agents include peroxides, most preferably hydrogen peroxide. Oxidizing agents can be delivered utilizing drug delivery balloon catheters. Preferred delivery catheters include an inflatable balloon having a perfusion lumen therethrough to allow for longer application periods. Oxidizing agents can be delivered either alone or in conjunction with radiation or stent delivery. One method includes local delivery of 0.1% hydrogen peroxide to a dilated stenosis wall for a period of 10 minutes at a rate of 0.5 cc per minute.

Each one of these patents, however, fails to teach in vivo electrochemical production of therapeutic agents.

There is thus a great need for and it would be highly advantageous to have methods, systems and devices for in vivo electrochemical production of therapeutic agents.

SUMMARY OF THE INVENTION

Hence, according to one aspect of the present invention, there is provided a method of producing a therapeutic agent in a body, the method comprising implanting an active metal in a tissue, for electrochemically converting at least one substance present in the body fluid into the therapeutic agent.

According to an additional aspect of the present. invention, electrochemically converting the at least one substance present in the body fluid into the therapeutic agent comprises direct conversion.

According to an additional aspect of the present invention, electrochemically converting the at least one substance present in the body fluid into the therapeutic agent comprises indirect conversion.

According to an additional aspect of the present invention, the at least one substance is a normal body fluid constituent.

According to an additional aspect of the present invention, the normal body fluid constituent is selected from the group consisting of water, molecular oxygen, nitrite and nitrate ions and L-arginine.

According to an alternative aspect of the present invention, the at least one substance is administered to the body.

According to an additional aspect of the present invention, the at least one substance is administered to the body through a diet.

According to an alternative aspect of the present invention, the at least one substance is administered to the body through a medical administration.

According to an additional aspect of the present invention, the at least one substance is selected from the group consisting of nitrite ion, nitrate ions, and a combination thereof.

According to an additional aspect of the present invention, the therapeutic agent is the vasodilating agent, nitric oxide (NO).

According to an alternative aspect of the present invention, the therapeutic agent is an oxidizing agent.

According to an additional aspect of the present invention, the oxidizing agent is selected from the group consisting of molecular chloride, perchloric acid, superoxide, ozone, molecular oxygen, singlet oxygen, hydroxyl radical, hypochlorite, hydrogen peroxide and a combination thereof.

According to an additional aspect of the present invention, the active metal comprises zinc.

According to an alternative aspect of the present invention, the active metal comprises iron.

According to an additional aspect of the present invention, implanting comprises implanting a stent formed of a biologically inert metal, fully coated with the active metal.

According to an alternative aspect of the present invention, implanting comprises implanting a stent formed of a biologically inert metal, having:

a portion coated with the active metal, operative as an anode; and an uncoated portion, operative as a cathode.

According to an additional aspect of the present invention, the implanting further comprises implanting the portion coated with the active metal, downstream of the uncoated portion, so that the therapeutic agents, produced at the cathode, will migrate downstream with the body fluid, to effect therapy at the anode as well.

According to an alternative aspect of the present invention, the coated and uncoated portions are equally distributed along the length and width of the stent.

According to an additional aspect of the present invention, the uncoated portion is further operative as a catalyst to the conversion.

According to an alternative aspect of the present invention, implanting comprises implanting a stent formed of a biologically inert material, wherein the stent includes a piece of the active metal attached thereto.

According to an additional aspect of the present invention, the stent is further operative as a catalyst to the conversion.

According to an alternative aspect of the present invention, implanting comprises implanting an anchor formed of a biologically inert metal, fully coated with the active metal.

According to an additional aspect of the present invention, implanting comprises implanting an anchor formed of a biologically inert metal, having:

a portion coated with the active metal, operative as an anode; and an uncoated portion, operative as a cathode.

According to an additional aspect of the present invention, the implanting further comprises implanting the portion coated with the active metal, downstream of the uncoated portion, so that the therapeutic agents, produced at the cathode, will migrate downstream with the body fluid, to effect therapy at the anode as well.

According to an alternative aspect of the present invention, the coated and uncoated portions are equally distributed along the length and width of the anchor.

According to an additional aspect of the present invention, the uncoated portion is further operative as a catalyst to the conversion.

According to an alternative aspect of the present invention, implanting comprises implanting an anchor formed of a biologically inert material, wherein the anchor includes a piece of the active metal attached thereto.

According to an additional aspect of the present invention, the anchor is further operative as a catalyst to the conversion.

According to an additional aspect of the present invention, the tissue is a blood vessel.

According to an additional aspect of the present invention, the tissue is a renal artery.

According to an alternative aspect of the present invention, the tissue a brain tissue.

According to an alternative aspect of the present invention, the tissue is a cancerous tissue.

According to an alternative aspect of the present invention, the tissue is a blood vessel feeding a cancerous tissue.

According to an alternative aspect of the present invention, the tissue is a blood vessel feeding a tissue for which therapeutic treatment is desired.

According to another aspect of the present invention, there is provided a method, comprising implanting an active metal in the body, for electrochemically converting at least one substance, present in the body, into the oxidizing agent.

According to another aspect of the present invention, there is provided a method, comprising implanting an active metal in the tissue, for electrochemically converting at least one substance, present in the body fluid, into an oxidizing agent, in an amount sufficient for reducing cell proliferation in the tissue.

According to another aspect of the present invention, there is provided a method, comprising implanting an active metal in a tissue, for electrochemically converting at least one substance present in the body fluid into the vasodilating agent, nitric oxide.

According to another aspect of the present invention, there is provided a medical implant for producing a therapeutic agent in a body, the medical implant comprising an active metal for electrochemically converting in a body fluid stream environment, at least one substance present in the body fluid into the therapeutic agent.

According to another aspect of the present invention, there is provided an implanted vessel, comprising an active metal, for electrochemically converting in a body fluid stream environment, at least one substance present in the body fluid into the therapeutic agent. The present invention successfully addresses the shortcomings of the presently known configurations by providing a device and method for spontaneous electrochemical production of therapeutic species, within a tissue, by implanting in the tissue an active metal, which undergoes corrosion, thus acting as a reducing agent to constituents in the tissue, so as to cause these constituents to form the therapeutic agents.

Unless otherwise defined, all technical and scientific terms used herein have the same meanings as are commonly understood by one of ordinary skill in the art to which this invention belongs. Although methods and materials similar or equivalent to those described herein can be used in the practice or testing of the present invention, suitable methods and materials are described herein.

In case of conflict, the patent specification, including definitions, will prevail. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 7A-7D are schematic illustrations of implantable vessels, in accordance with another preferred embodiment of the present invention.

DESCRIPTION OF THE PREFERRED EMBODIMENTS

The present invention is of a device and method for spontaneous electrochemical production of therapeutic species, within a tissue. Specifically, the present invention relates to implanting in the tissue an active metal, which undergoes corrosion, thus acting as a reducing agent to constituents in the tissue, so as to cause these constituents to form the therapeutic agents.

The principles and operation of the device according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 1:
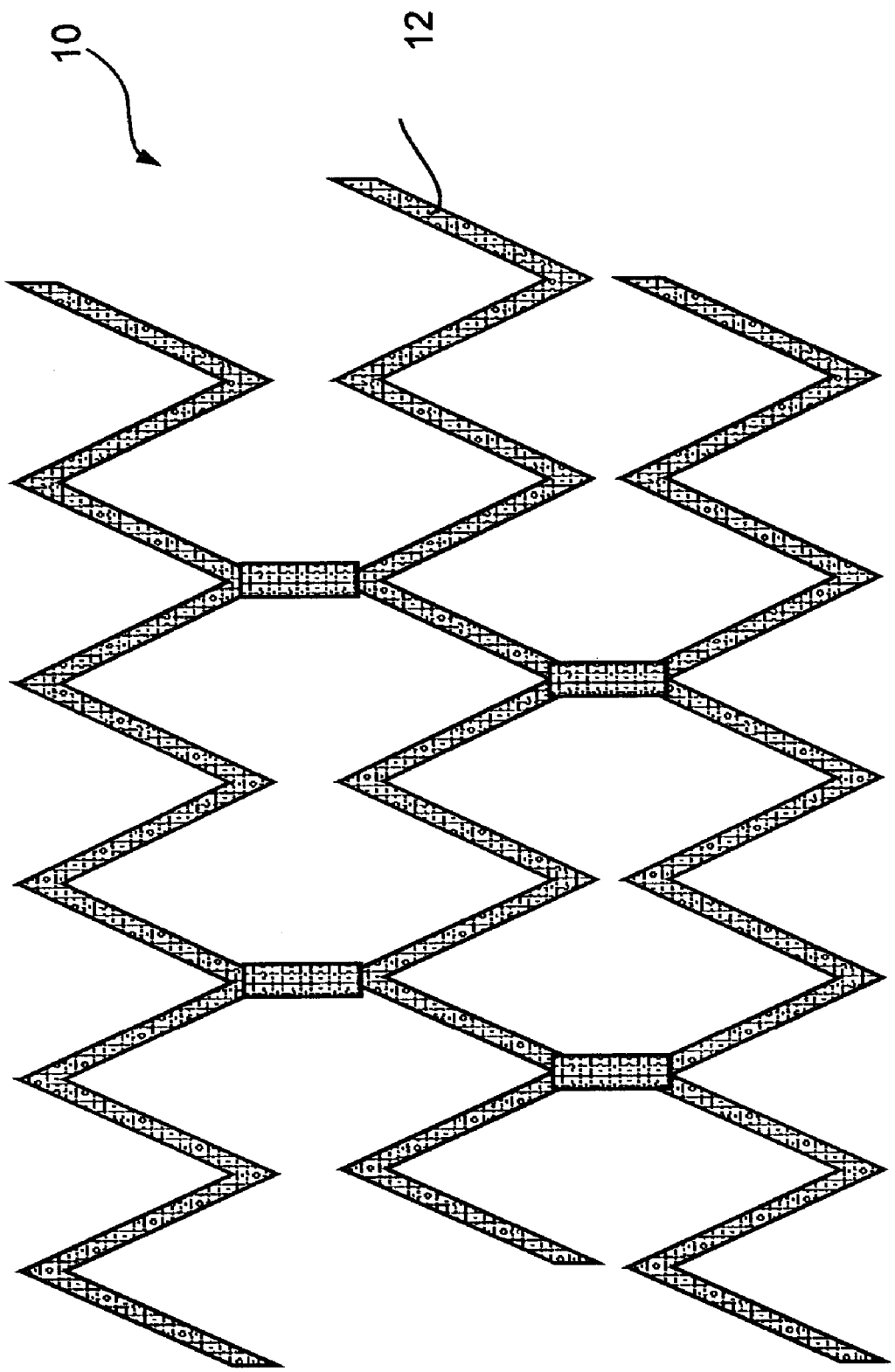
FIG. 1 is a schematic illustration of a stent, coated with an active metal, in accordance with another preferred embodiment of the present invention.

Referring now to the drawings, FIG. 1 is a schematic illustration of an implant 10, formed as a stent 10, fully coated with an active metal 12, in accordance with a first preferred embodiment of the present invention. An active metal in the present context is a metal that will corrode in the body environment, and thus act as a reducing agent. Active metal 12 may be for example, zinc. Alternatively, it may be iron.

Stent 10 is adapted for implantation in a blood vessel, where active metal 12 will corrode and act as a reducing agent for blood constituents, and (or) other body fluid constituents, as will be described hereinbelow, in conjunctions with Examples 1-8. In accordance with the first preferred embodiment of the present invention, stent 10 is homogeneous, and operative as an anode and a cathode, wherein both oxidation and reduction reactions occur on its surface. In the absence of a catalyst, such as platinum, the corrosion reaction is relatively slow. Thus the first preferred embodiment of the present invention is applicable to situations, where a slow reaction rate is preferred.

Preferably, stent 10 is operative as a reducing agent, water and molecular oxygen, leading to the production of hydrogen peroxide and hydroxide ions. These can be used to prevent unwanted cell proliferation in cases of, for example, cancer, stenosis, restenosis, in-stent stenosis, and in-graft stenosis. Their production by stent 10 is particularly useful for treatment of in-stent stenosis.

Additionally or alternatively, stent 10 is operative as a reducing agent to nitrite and nitrate ions, and L-arginine, leading to the production of the vasodilating agent nitric oxide (NO). Nitric oxide may be operative to dilate blood vessels. In particular, stent 10 may be placed in the renal artery, and the production of nitric oxide may enlarge renal blood vessels and blood capillaries. However, it will be appreciated that for significant production of nitric acid, nitrite and nitrate ions may need to be administered to the body, by diet, or intravenously.

As will be described hereinbelow, in conjunction with Examples 1-8, some reduction reactions are a single-step reduction process, so the electrochemical conversion of a substance into a therapeutic agent may be considered a direct conversion. Other reduction reactions include two or more steps, so the electrochemical conversion of a substance into a therapeutic agent may be considered indirect conversion.

It will be appreciated that since the active metal undergoes depletion, the therapeutic nature of the present invention is temporary.

Figure 2:
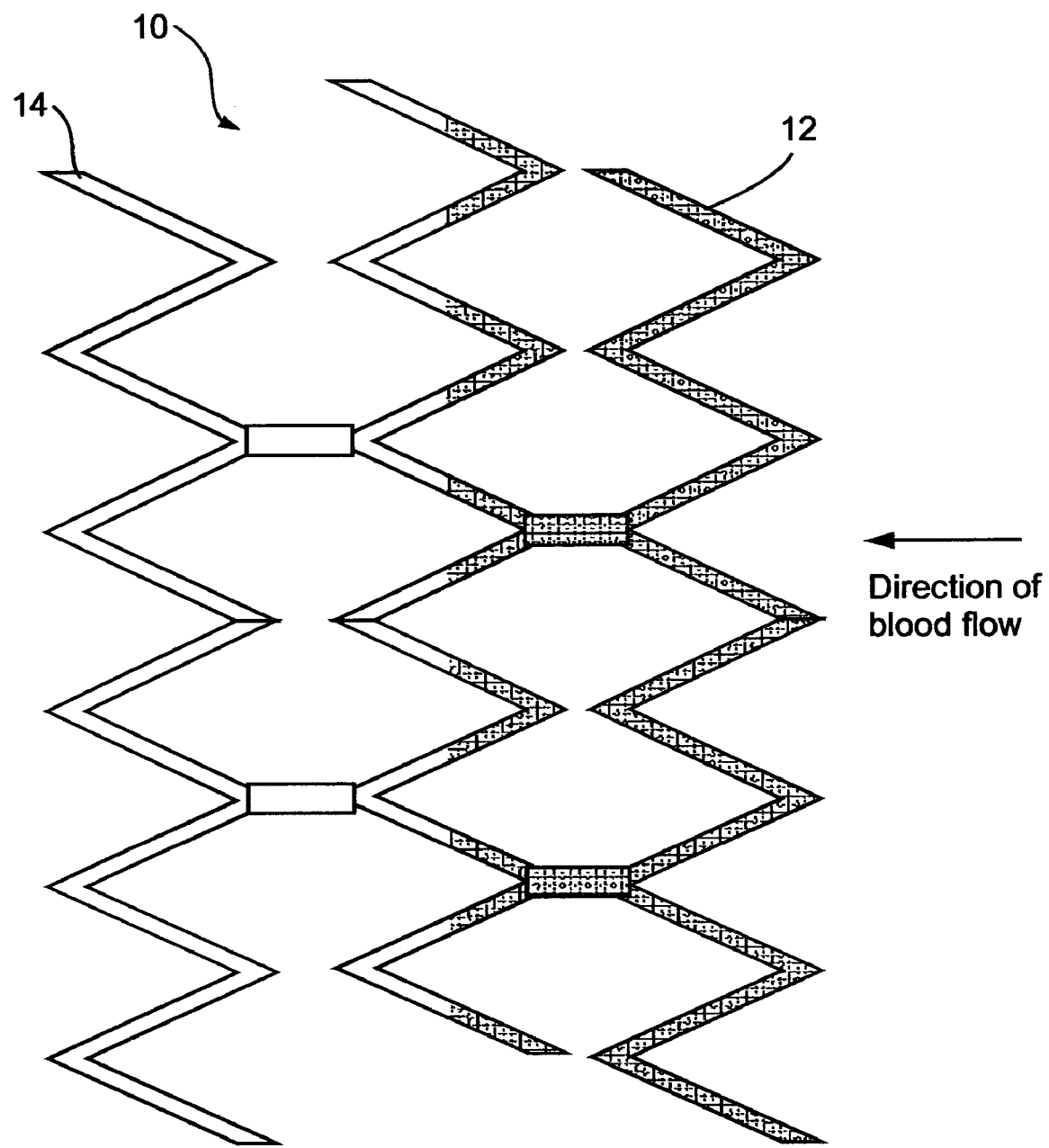
FIG. 2 is a schematic illustration of a stent, partially coated with an active metal, in accordance with another preferred embodiment of the present invention.

Referring further to the drawings, FIG. 2 is a schematic illustration of implant 10, formed as stent 10, formed of a platinum body 14, and partially coated with active metal 12, in accordance with a second preferred embodiment of the present invention. In this situation, the portion coated with active metal 12 acts as an anode while the portion formed of bare platinum body 14 acts as a cathode. In the presence of platinum, which acts as a catalyst, the corrosion reaction is considerably faster than that described in conjunction with FIG. 1. In accordance with the present embodiment, stent 10 is disposed with the cathode upstream of the anode, so that therapeutic compounds produced at the cathode, will migrate downstream with the blood, to effect therapy at the anode as well.

It will be appreciated that another biologically inert metal, operative as a catalyst, may be used for the cathode, in place of platinum. For example, palladium, iridium, nickel, a platinum-iridium alloy, or other alloys thereof may be used.

It will be appreciated that a biologically inert metal, which is a relatively poor catalyst, may still be used for the cathode, in place of platinum. For example, stainless steel, gold, or a gold alloy may be used. The use of a poor catalyst, such as stainless steel, will slow down the reaction, when compared to the use of platinum.

It will be appreciated that a biologically inert material, which is inoperative as a cathode, may still be used for the stent body, in place of platinum. For example, titanium, tantalum, alloys thereof, as well as various other materials such as a high-strength, high-resilience plastic may be used. The use of these materials will create a situation wherein active metal 12 is operative both as an anode and as a cathode, similar to the situation described in context of FIG. 1.

It will be appreciated that a combination of three or more materials may also be used in stent 10.

Figure 3:
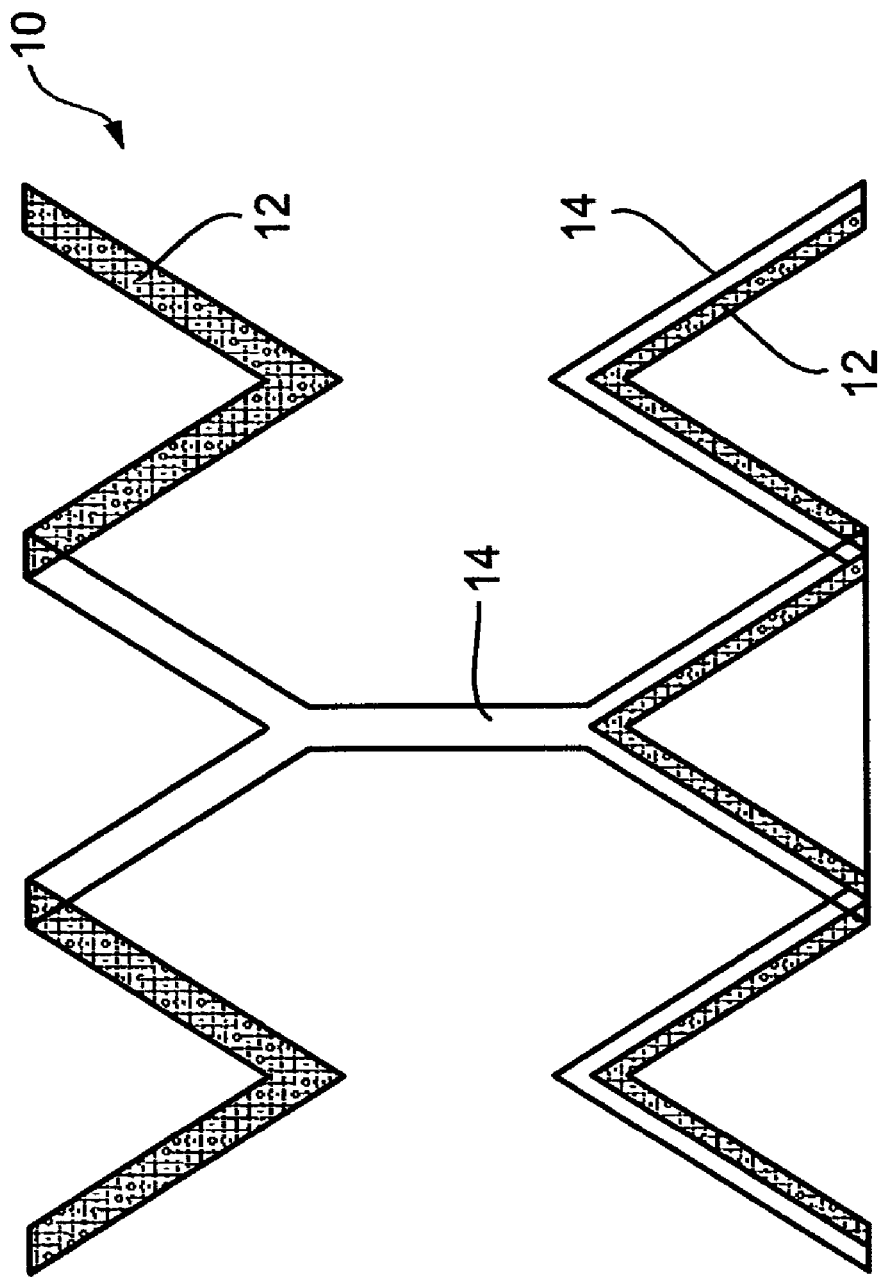
FIG. 3 is a schematic illustration of a stent, partially coated with an active metal, in accordance with another preferred embodiment of the present invention.

Referring further to the drawings, FIG. 3 is a schematic illustration of implant 10, formed as stent 10, formed of platinum body 14, and partially coated with active metal 12, in accordance with a third preferred embodiment of the present invention. In accordance with the present embodiment, the portions of bare platinum body 14 and active metal coating 12 are evenly distributed along stent 10. Alternating coating patterns may also be employed, generating a plurality of alternating cathodes and anodes. In these manners, the therapeutic compounds produced at the cathode generally reach all portions of stent 10, in a manner somewhat similar to that of FIG. 1.

The current density on the uncoated portions of the stent may not be uniform—it will be the highest in regions of contact between the coated and the uncoated portions, where the electrolytic path between the anodic and the cathodic sections of the surface is the shortest, which amounts to the lowest internal resistance of the local cells. A non-uniform current distribution may, in fact, be useful to create the highest concentration of therapeutic species, where restenosis is expected to be the most severe.

The total amount of zinc coated can be chosen to ensure that the electroless reduction occurs just as long as desired. The rate of corrosion of the zinc will depend on the location of the stent, the flow rate and the amount of oxygen in the blood, as well as on the nature of the metal of which the stent has been constructed.

It will be appreciated that with time, the situation of FIG. 1 hereinabove, will resemble that of FIG. 3, due to active metal depletion.

Figure 4:
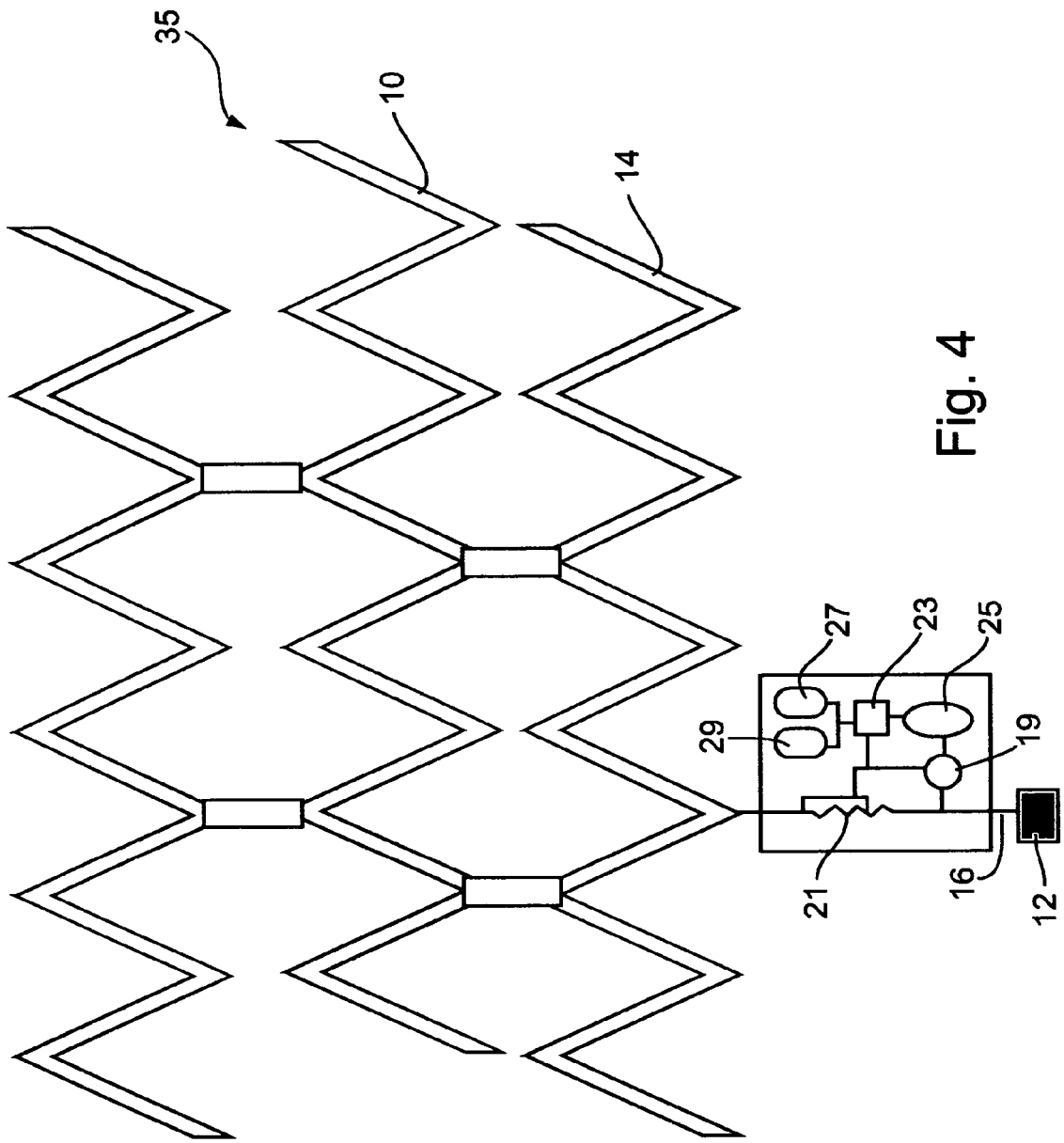
FIG. 4 is a schematic illustration of a stent, to which a strip of active metal is attached, in accordance with another preferred embodiment of the present invention.

Referring further to the drawings, FIG. 4 is a schematic illustration of an implant 35, which includes stent 10, formed of bare platinum body 14, in accordance with a fourth preferred embodiment of the present invention. Additionally, implant 35 includes a strip of active metal 12. An electronic conductor, such as a metal wire 16, connects active metal 12, forming the anode, and bare platinum body 14, forming the cathode.

There are several reasons for metal wire 16 of implant 35, as follows:

i. The anode and cathode may be implanted at different locations, for example, as will be described hereinbelow, in conjunction with FIGS. 6A and 6B.

ii. By providing an ammeter 19, or an equivalent thereof, in electrical communication with metal wire 16, the current through metal wire 16 may be measured, for providing an indication of the reaction rate.

iii. Additionally, by adding a variable resistor 21, controlled by a controller 23, wherein controller 23 is in signal communication with ammeter 19, and by adding a power source 25, one could control the current through metal wire 16, hence, the reaction rate, responsive to measurements of ammeter 19. Power source 25 may be, for example, a miniature battery. Miniature body implantable batteries are well known in the art. Such batteries are used, for example, for powering pace-makers and other devices and sensors implanted in the body.

iv. By adding a receiver 27 and a transmitter 29, in signal communication with controller 23, an extracorporeal station could receive signals, indicative of the reaction rate, as measured by ammeter 19, and transmit signals for varying the resistance of resistor 21, preferably responsive to the reaction rate signals.

v. By providing a telemetric energy transfer, battery 25 may be recharged. Telemetric energy transfer according to the present invention can be effected in any one of a plurality of ways known in the art, including radio frequency energy transfer, magnetic energy transfer and acoustic energy transfer.

Radio frequency energy transfer can be effected, for example, using an antenna coil and a rectifying circuit. Such circuits are well known and in common use in pacemakers and defibrillators, and therefore require no further description herein.

Magnetic energy transfer can be effected, for example, using a magnetic transducer which employs a magnet and a coil as is well known in the art. Examples of magnetic energy transfer are disclosed in, for example, U.S. Pat. Nos. 5,880,661, 6,185,457, 6,167,307, 6,164,284 and 6,162,238, which are incorporated herein by reference.

Acoustic energy transfer can be effected, for example, using an acoustic transducer as described, for example, in U.S. Pat. Nos. 6,140,740 and 6,170,488, which are incorporated herein by reference.

Telemetry can also be used, according to the present invention, to transmit data pertaining to the implant and (or) its effect from within the body outside thereof, for example as taught by U.S. Pat. No. 6,277,078, U.S. patent application Ser. No. 09/872,129 now U.S. Pat. No. 6,486,588 and U.S. patent application Ser. No. 09/690,615 now U.S. Pat. No. 6,628,989 whose disclosures are incorporated herein by reference.

Thus, implant 35 of the present invention may employ telemetry for accomplishing powering, control and/or communication of data. Different type telemetry can be employed for effecting each of these criteria.

In case telemetry is employed, an extracorporeal unit is provided, designed and constructed for powering, interrogating, controlling and/or receiving data from the implant.

Figure 5:
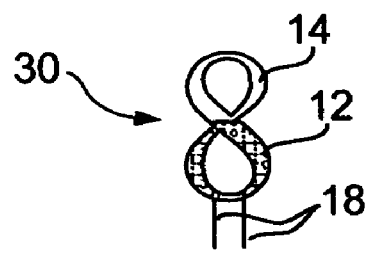
FIG. 5 is a schematic illustration of an anchor, partially coated with an active metal, in accordance with another preferred embodiment of the present invention.

Referring further to the drawings, FIG. 5 is a schematic illustration of an anchor 30, formed of platinum body 14, and partially coated with an active metal 12, in accordance with another preferred embodiment of the present invention. Anchor 30, which includes anchoring pins 18, or other means of anchorage, may be implanted in tissue other than the blood vessel, for example, in the brain, or within a cancerous tissue. When implanted in the brain, a brain fluid known as cerebrospinal fluid (CSF) is operative as the electrolyte for the electrochemical reaction. When implanted in cancerous tissue, or another tissue, the interstitial fluid is operative as the electrolyte for the electrochemical reaction. It will be appreciated that anchor 30 may be implanted also in the stomach, the intestines, and other body cavities and organs, such as the bladder cavity.

Figure 6A:
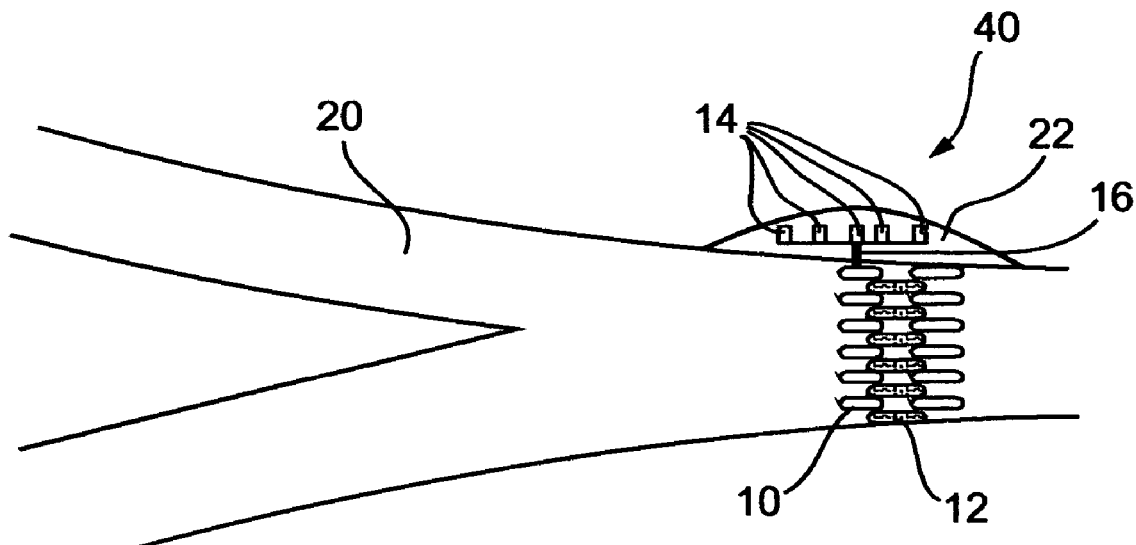
FIGS. 6A and 6B are schematic illustrations of an implant, adapted for cancer treatment, in accordance with another preferred embodiment of the present invention.
Figure 6B:
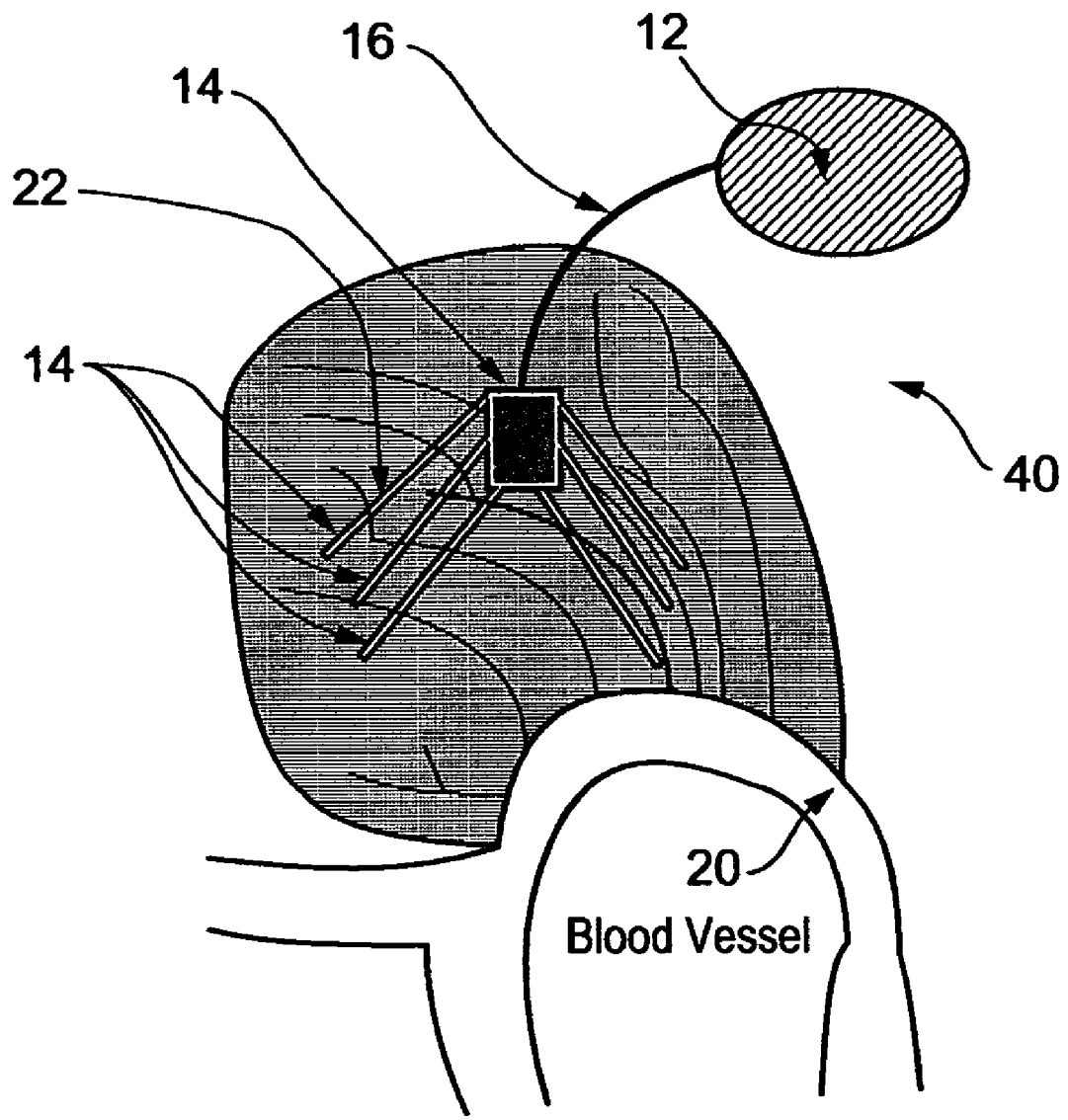

Referring further to the drawings, FIGS. 6A and 6B are schematic illustrations of implants 40, adapted for cancer treatment, in accordance with another preferred embodiment of the present invention. Preferably, implant 40 is formed of stent 10, fully coated with an active metal, and operative as an anode, adapted for implantation in a blood vessel 20 which feeds a tumor 22. At least one cathode, preferably formed of bare platinum 14, is implanted within tumor 22. Additionally, a plurality of cathodes of bare platinum 14, may be implanted, for a better distribution of the therapeutic compounds. Uniform production and concentration of the therapeutic compound in the tumor will ensure that all the tumor will be treated with minimal side effect on the healthy tissue and organ around it. The interstitial fluid is operative as the electrolyte for the electrochemical reaction, producing therapeutic agents within the tumor.

Referring further to the drawings, FIGS. 7A-7D are schematic illustrations of implantable vessels 50, in accordance with another preferred embodiment of the present invention. The problem of restenosis is not limited to stents, rather it is also characteristic of implantable vessels, including artificial or natural grafts such as by-pass grafts of veins or arteries, and shunts. Thus, an implantable vessel 50 includes a vessel body 51, defining a flexible tube. Body 51 may be an artificial body, made of an acceptable material such as ePTFE or Dacron. However, vessel 50 may also be a natural blood vessel, obtained for, example from the lungs or the, leg.

As seen in FIGS. 7A and 7B, body 51 includes a metal mesh 17, formed of bare platinum 14 wires, operative as cathodes, and zinc coated wires 12, operative as anodes.

Alternatively, as seen in FIGS. 7C-7C, body 51 includes a metal mesh 15, formed of bare platinum 14 wires, operative as cathodes. A zinc anode, may be located outside body 51, connected to cathodes 14 via wire 16.

It will be appreciated that a single zinc wire, or a pair of zinc and platinum wires, connected by a metal wire, or a stent, or a ring, fully or partly coated with zinc may also be used with the implantable vessel. It will be appreciated that other geometries are similarly possible.

It will be appreciated that another active metal, such as iron, may be used for the anode, and another inert metal may be used for the cathode, as has been described hereinabove.

Figure 8:
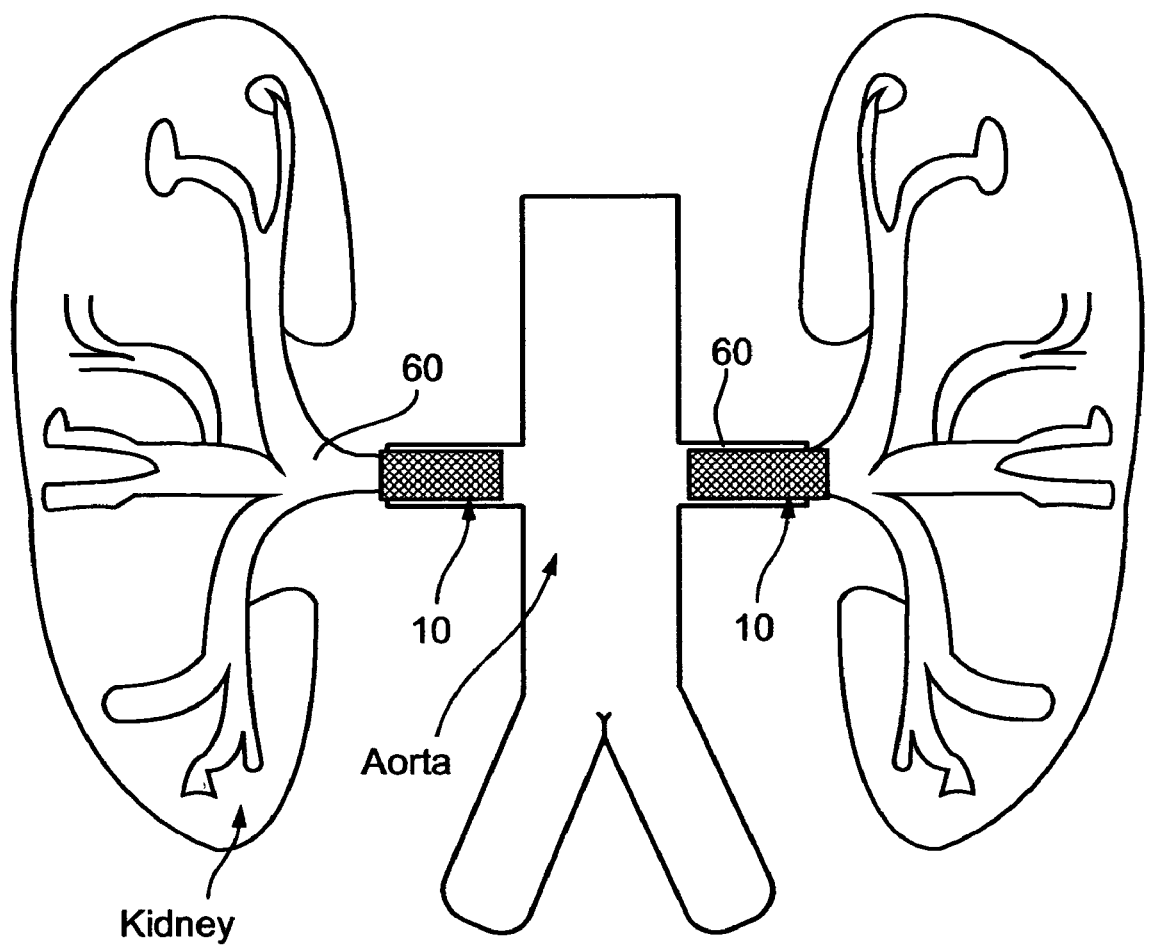
FIG. 8 is a schematic illustration of a stent, coated with an active metal, at the renal arteries, in accordance with the present invention.

Referring further to the drawings, FIG. 8 is a schematic illustration of a stent 10, coated with an active metal, at renal arteries 60, in accordance with the present invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Example 1

Open-Circuit Corrosion

When an active metal, such as zinc or iron, is placed in solution, it tends to corrode, by the anodic dissolution of the metal, for example, $$Zn \rightarrow Zn^{2+} + 2e^- \qquad [1]$$

This process cannot continue for any significant length of time, without a suitable cathodic process, in which the electrons are consumed. In blood and other physiological fluids the typical pH is 7.4. Thus, the cathodic process may be described as:

$$O_2 + 2H_2O + 4e^- \rightarrow 4(OH)^- \qquad [2]$$

The average potential measured vs. a suitable reference electrode will be somewhere between the reversible potentials for the anodic and the cathodic reactions. However, on the atomic scale, there will be sites on which the anodic reaction will take place and others on which the cathodic reaction will occur.

Zinc or iron are the preferred active metals for the present invention, because their reversible potentials are sufficiently negative and because they both exist naturally in blood and a small increase in their concentration is unlikely to be physiologically damaging or poisonous.

Example 2

Electroless In-Vivo Reduction of $NO_2^-$ and $NO_3^-$

The appropriate reactions for the anions of nitrous acid (the nitrate, $NO_3^-$) and nitric acid, (the nitrite, $NO_2^-$), and their reversible potentials in the blood and other body fluids, at pH=7.4, are given below.

$$NO_2^{31} + H_2O + e^- \rightarrow NO + 2(HO)^- \quad E=0.329V \text{ vs. SHE} \qquad [3]$$

$$NO_3^{31} + 2H_2O + 3e^- \rightarrow NO + 4(HO)^- \quad E=0.350 \text{ V vs. SHE} \qquad [4]$$

If an active metal such as zinc or iron is attached to a stent and corrodes, as described in Equation [1], either one of the above reactions could take part in the corrosion process, as the cathodic reaction. In principle, Equations [3] and [4] may be considered single-step reduction processes, so that the electrochemical conversion is direct.

Oxygen reduction (Equation [2], as well as the equations of Example 3, hereinbelow) may also occur in parallel with Equations [3] and [4], so that the current efficiency for the reduction of the nitrogen-containing anion will probably be less than unity. This process may be called electroless in-vivo reduction.

Example 3

In-Vivo Electrochemical Production of Hydrogen Peroxide

Thermodynamically, oxygen reduction should lead to the formation of water. However, the high activation energy of the reaction makes it less favored, when compared with competing reactions, though thermodynamically unstable, as follows:

$$O_2 + 2H_2O + 2e^- \rightarrow H_2O_2 + 2(OH)^- \quad [5]$$

This reaction may then be followed by the reaction:

$$H_2O_2 + 2e^- \rightarrow 2(OH)^- \quad [6]$$

In this instance, one may consider the products of reaction [5] direct, while the product of reaction [6], the second-step reaction, indirect.

The following discussion analyzes and compares the thermodynamics and the kinetics of reaction [5] and [6], which lead to the presence of $H_2O_2$ in aquatious solutions, with those of alternative reactions, which may be thermodynamically stable, but kinetically very slow to proceed.

The other reaction that can take place and is relevant in the present context, although as pointed out, it is very slow, kinetically, is:

$$O_2 + 2H_2O + 4e^- \rightarrow 4(OH)^- \quad [7]$$

In addition, the following process, in which molecular hydrogen is formed, can occur at sufficiently negative potentials, but it is thermodynamically unfavored at a pH of 7.4, and in the presence of dissolved oxygen and other reducible materials, such as nitrite and nitrate ions:

$$2H_2O + 2e^- \rightarrow 2(OH)^- + H_2 \quad [8]$$

The corresponding standard reduction potentials at pH=0 and at the body pH of 7.4 are:

| Equation | Reaction | $E^0$ (volt SHE) at pH = 0 | $E^0$ (volt SHE) at pH = 7.4 |
|---|---|---|---|
| [9]  | Reduction of $H_2O_2$ to $H_2O$ | 1.776 | 1.339 |
| [10] | Reduction of $O_2$ to $H_2O_2$  | 0.682 | 0.245 |
| [11] | Reduction of $O_2$ to $H_2O$    | 1.229 | 0.792 |
| [12] | Reduction of $H_2O$ to $H_2$    | 0.000 | -0.437 |

It follows from these data that hydrogen peroxide is not stable thermodynamically in water. To further demonstrate this, one may add reaction [6] with the reverse of reaction [5]:

$$H_2O_2 + 2e^- \rightarrow 2(OH)^- \quad E^0 = 1.339V \quad [6]$$

$$H_2O_2 \rightarrow O_2 + 2H^+ + 2e^- \quad E^0 = -0.245V \quad [\text{reverse of 5}]$$

$$2H_2O_2 \rightarrow O_2 + 2H_2O; \quad \Delta E^0 = 1.094V \quad [13]$$

From thermodynamic considerations, the self-decomposition reaction of hydrogen peroxide (Equation [9]) is favored, since:

$$\Delta G^0 = -nF\Delta E^0 = -211 kj/mole \quad [14]$$

Specifically, is should not be possible to make and maintain an appreciable concentration of hydrogen peroxide in aqueous solution. At the positive electrode water is oxidized to hydrogen peroxide at 1.339 V (at pH=7.4), while hydrogen peroxide is oxidized to molecular oxygen at a much lower potential of 0.245 V. In other words, at the potential at which it is formed from water, $H_2O_2$ is highly unstable with respect to its further oxidation to $O_2$.

The relative stability of this compound in water is primarily due to the slow kinetics of its decomposition. This is not surprising, considering that during the reaction described in Equation [13], two H—O bonds are broken in one molecule and an O—O bond is broken in another. It also follows from Equation [13] that the rate of self-decomposition, which is a bi-homomolecular reaction, will decrease with dilution, as is well known experimentally.

Similarly, at the negative electrode, oxygen can be reduced to hydrogen peroxide at a potential of 0.245 V, where it is highly unstable towards further reduction to water, which can occur already at a potential of 1.339 V. This is a direct consequence of the thermodynamic instability of $H_2O_2$.

However, the kinetics of the different reactions plays a decisive role. In practice $O_2$ is reduced in two stages. A two-electron reduction step to $H_2O_2$ (Equation [5]) followed by another two-electron reduction step of the peroxide to $(OH)^-$ (Equation [6]). The slow kinetics of the second step (Equation [6]), or alternative step (Equation [7]) is not surprising. In Equation [5] two protons are attached to an oxygen molecule following charge transfer, but no bonds are broken. In Equations [6] and [7] the O—O bond must be broken. Indeed, one of the challenges facing the development of practical fuel cells is to develop efficient (and inexpensive) catalyst that can promote the reduction of oxygen to water and prevent its termination at the peroxide stage.

Hydrogen evolution (Equation [8]) can be a relatively fast reaction, comparable to or even faster than the reduction of $O_2$ to $H_2O_2$. However, its reversible potential is 0.682 V more negative. Therefore oxygen reduction to peroxide is found to occur first. The second reduction wave of oxygen (Equation [6]), associated with the reduction of $H_2O_2$ that is formed as an intermediate step, is at a high overpotential in the region of hydrogen evolution and can occur before, together with, or after the onset of hydrogen evolution.

In summary, the sequence of reactions occurring at the cathode in an aqueous solution containing oxygen is:

$$O_2 \rightarrow H_2O_2 \rightarrow H_2O \rightarrow H_2 \quad [15]$$

If the current density applied is small and the concentration of oxygen in the solution is high enough, so that its concentration at the cathode surface is not significantly depleted, the first step, i.e., the production of $H_2O_2$ and the reduction of nitrite and nitrate to nitric oxide will probably be the main processes taking place at the cathode.

Example 4

Electrode Kinetic Considerations

Given an active metal, such as zinc, immersed in an electrolyte, operative as an anode, different second electrode selections and configurations will effect the reaction rate, as follows:

i. When no second electrode is provided, the anodic and the cathodic reactions occur on different parts of the active-metal surface, perhaps at locations very close to each other, but possibly further away, depending on the degree of inhomogeneity of the surface. This situation is illustrated in FIG. 1.

ii. When a second electrode, such as stainless steel, which is not a catalyst, is provided, for example, when a stent, formed of stainless steel, is partly coated with an active metal, the cathodic reaction may take place on the second electrode. However, the reaction rate will not be substantially affected by the presence of the second metal.

iii. When a second electrode, such as platinum, which is a known catalyst, is provided, for example, when a stent, formed of platinum, is partly coated with an active metal, with no electrical insulation between the two metals, the cathodic reaction will be preferential to the second electrode, and the reaction rate will greatly increase. This situation is illustrated in FIGS. 2 and 3.

iv. When a second electrode, whether operative as a catalyst or not (e.g., platinum or stainless steel) is provided, connected by an electronic conductor, such as a variable resistor, to the active metal, the reaction rate may be controlled, by controlling the rate of electron transfer between the cathode and the anode. This situation is illustrated in FIG. 4.

It will be appreciated that combinations of the above are possible.

It will be appreciated that the stent or anchor may be formed of inert materials that do not participate in the reactions and an anode, or an anode and a cathode, which may be further operative as a catalyst, may be attached to the stent or anchor.

Example 5

The Rate of Corrosion of an Active Metal in the Blood

The rate of the active metal corrosion determines the concentration of the electrochemical reaction products. The rate is controlled by the reversible potential of the metal at the given condition and by the reactant concentration (e.g., dissolved oxygen).

The following corrosion rate estimation is given for zinc, although other active metals can be used, such as iron.

The standard reversible potential for the $Zn^{+2}/Zn$ couple is $-0.76$ volts versus SHE (Standard Hydrogen Electrode). The reversible potential will depend on the concentration in the solution according to the Nernst equation. It is common, in considering corrosion problems, based on the Pourbaix's potential—pH diagrams, to assume that the concentration of the corrosion product ($Zn^{+2}$ in the present case) is 1 micro molar. The reversible potential will be:

$$E_{rev} = E_0 + (0.0295 RT) \log |Zn^{+2}51 = -0.937 \text{ SHE} \quad [16]$$

The above is independent of pH. For the reduction of $O_2$ to $H_2O_2$ at pH=7.4, one has $E_{rev}$=0.68 V and for $NO_3^-$ $E_{rev}$=0.350 V.

As will be shown, the open circuit corrosion potential will be very close to the reversible potential for zinc, perhaps less than 50 mV anodic to it. At such a negative potential, the reduction of both oxygen and the nitrate ion will be almost equal to the rate of anodic dissolution of the metal.

The concentration of oxygen and nitrate in the blood are approximately 0.13 mM and 0.038 mM respectively. The diffusion coefficient of oxygen is $2 \times 10^{-5}$ cm$^2$/s. That of nitrate is probably somewhat lower, but since this ion is at a lower concentration, one can use the same value for both species as a good approximation.

The limiting current density will be given by:

$$i = \frac{FD(n_{o_2} C_{o_2} + n_{NO_3^-} C_{NO_3^-})}{\delta} \quad [17]$$

The Nernst diffusion-layer thickness, $\delta$, depends on many factors, including the rate of flow of the blood and the accumulative deposition of cells or any other substance, such as blood proteins that may cover the surface. A value of 0.01 cm is a good estimate for a bare surface. Using this value yields:

$$i = \frac{96.485 \cdot 10^3 \times 2 \cdot 10^{-5} \times (2 \times 1.3 \cdot 10^{-7} + 3 \times 0.38 \cdot 10^{-7})}{1 \cdot 10^{-2}} = \quad [18]$$
$$72.2 \cdot 10^{-6} \text{ A/cm}^2$$

Converting this rate into mg/cm$^2$sec results in:

$$72 \text{ μA/cm}^2 = \frac{72 \cdot 10^{-6}}{96.485 \cdot 10^3} \times 32.7 = 24.4 \cdot 10^{-9} \text{ gr/cm}^2 \text{ sec} \quad [19]$$

This value corresponds to a rate of about 2.1 mg/cm$^2$ in a 24 hour period.

Note that this is only a gross estimation. The actual rate of zinc dissolution will be probably lower than the calculated value. The reasons for that are twofold. First, the diffusion coefficient in blood is lower than the values based on diffusion in diluted aqueous solution. Second, cells, platelets and proteins may cover metallic surfaces, resulting in a reduction of the reactants (oxygen and nitrate) flow rate and (or) their diffusion rate.

Example 6

An Estimate of the Concentration of NO Produced at the Surface of the Stent

The total rate of corrosion, according to Equation [18], is $72.2 \times 10^{-6}$ A/cm$^2$. Assuming that all of this current is consumed in the 1-electron reduction of $NO_2^-$ to NO, the rate of production of NO will be:

$$\frac{72.2 \times 10^{-6}}{96.5 \times 10^3} = 0.76 \times 10^{-9} \text{ mole/s} = 22.6 \times 10^{-9} \text{ g/s} \quad [20]$$

The diffuse double layer thickness at the surface is given by:

$$\delta = \sqrt{\pi D t} \quad [21]$$

Using the values of D=$2 \times 10^{-5}$ cm$^2$/s and t=1 sec, one gets, $\delta = 8 \times 10^{-3}$ cm, hence the average concentration of NO in the surface layer will be:

$$22.6 \times 10^{-9} / 8 \times 10^{-3} = 2.86 \text{ ppm} \quad [22]$$

Note that if the source of NO will be the nitrate ion $NO_3^-$, the above number will be divided by three, since three electrons are needed to reduce each nitrate ion to NO, while only one electron is needed to reduce a nitrite ion to NO.

Example 7

Zinc-Coated Coronary Stent

Taking a typical coronary stent 15 mm long expanded to 3 mm diameter with a metal coverage percentage of 15%. This stent has a metallic surface area of:

$$S_{stent} = \pi \cdot D \cdot L \cdot 2 \cdot 0.15 = 0.424 \text{ cm}^2 \quad [23]$$

where:
$S_{stent}$ is the stent internal and external surfaces;
D is the stent diameter; and
L is the stent length.

The rate of zinc dissolution from the surface of such a device (assuming a corrosion rate calculated in Equation [19]) results in:

$$\text{Rate} = (24.4 \times 10^{-9} \text{ gr/cm}^2\text{s}) \times (0.424 \text{ cm}^2) = 1.0 \times 10^{-8} \text{ gr/s} \quad [24]$$

Assuming that the stent will be coated with 40 μm of zinc (density=7.14 gr/cc) resulting in a total of:

$$W_{Zn} = 0.424 \times 40 \times 10^{-4} \text{ cm}^3 \times 7.14 \text{ gr/cm}^3 = 12 \text{ mg} \quad [25]$$

⇓

$$T_{corrosion} = 12 \cdot 10^{-3} / 1.0 \cdot 10^{-8} \text{ s} = 1.2 \cdot 10^6 \text{ s} \approx 14 \text{ days}$$

Corrosion rate=1×10⁻⁸ gm/s=8.6×10⁻⁴ gm/d≈1 mg/d [26]

It will be appreciated in this context that by selecting the amount of active metal, one can control the time by which electrode depletion will result is cessation of the reactions.

Example 8

Biological Effect of the Dissolved Metal

Zinc is an essential element in our diet. Too little zinc can cause health problems, but too much zinc is also harmful.

Based on the Agency for Toxic Substances and Disease Registry (ATSDR). 1994, Toxicological profile for zinc, (Atlanta, Ga.: U.S. Department of Health and Human Services, Public Health Service), the recommended dietary allowance (RDA) for zinc is 15 milligrams a day for men; 12 mg/day for women; 10 mg/day for children; and 5 mg/day for infants. Insufficient zinc in one's diet can result in a loss of appetite, a decreased sense of taste and smell, slow wound healing and skin sores, a damaged immune system, poorly developed sex organs, in men and growth retardation of fetuses.

Too much zinc, however, can also be damaging to one's health. Harmful health effects generally begin at levels from 10-15 times the RDA (in the 100 to 250 mg/day range). As can be appreciated the zinc amount released by the implant is far lower than these levels. Thus, a systemic or a local damage due to a high zinc level is highly improbable.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of producing a therapeutic agent in a body, the method comprising:
electrochemically converting at least one substance present in a body fluid flowing in a body lumen into a therapeutic agent by implanting a tubular implant in the body lumen, the implant comprising an uncoated portion and a coated portion, the coated portion coated with an active metal, for electrochemically converting at least one substance present in a body fluid flowing in the body lumen into a therapeutic agent, wherein the implant is implanted with the body lumen such that one of the uncoated portion and the coated portion is disposed upstream of the other relative to the flow of the body fluid in the body lumen, wherein the coated portion and the uncoated portion are directly exposed to the flow of body fluid.

2. The method of claim 1, wherein the electrochemically converting at least one substance present in the body fluid into the therapeutic agent comprises direct conversion.

3. The method of claim 1, wherein the electrochemically converting at least one substance present in the body fluid into the therapeutic agent comprises indirect conversion.

4. The method of claim 1, wherein the at least one substance is a normal body fluid constituent.

5. The method of claim 4, wherein the normal body fluid constituent is selected from the group consisting of water, molecular oxygen, nitrite and nitrate ions and L-arginine.

6. The method of claim 1, wherein the at least one substance is administered to the body.

7. The method of claim 6, wherein the at least one substance is administered to the body through a diet.

8. The method of claim 6, wherein the at least one substance is administered to the body through a medical administration.

9. The method of claim 6, wherein the at least one substance is selected from the group consisting of nitrite ion, nitrate ions, and a combination thereof.

10. The method of claim 1, wherein the therapeutic agent is an oxidizing agent.

11. The method of claim 1, wherein the therapeutic agent is nitric oxide.

12. The method of claim 1, wherein the active metal comprises zinc.

13. The method of claim 1, wherein the active metal comprises iron.

14. The method of claim 1, wherein the implant is a stent formed of a biologically inert metal, the coated portion operative as an anode, and the uncoated portion operative as a cathode.

15. The method of claim 14, wherein the implant is implanted with the portion coated with the active metal downstream of the uncoated portion, so that the therapeutic agents produced at the cathode migrate downstream with the body fluid to effect therapy at the anode.

16. The method of claim 14, wherein the coated and uncoated portions are equally distributed along a length and a width of the stent.

17. The method of claim 14, wherein the uncoated portion is further operative as a catalyst to the conversion.

18. The method of claim 1, wherein the implant is implanted with the coated portion downstream of the uncoated portion so that the therapeutic agents produced at the cathode migrate downstream with the body fluid to effect therapy at the anode.

19. The method of claim 1, wherein the uncoated portion is further operative as a catalyst to the conversion.

20. The method of claim 1, wherein the body lumen is a blood vessel.

21. The method of claim 1, wherein the body lumen is a renal artery.

22. The method of claim 1, wherein the body lumen is located in brain tissue.

23. The method of claim 1, wherein the body lumen is located in cancerous tissue.

24. The method of claim 1, wherein the body lumen is a blood vessel feeding a cancerous tissue.

25. The method of claim 1, wherein the body lumen is a blood vessel feeding tissue for which therapeutic treatment is desired.

26. The method of claim 1, wherein the uncoated portion is formed of biologically inert metal.

27. The method of claim 26, wherein the uncoated portion is operative as a cathode and the coated portion is operative as an anode.

28. The method of claim 27, wherein the implant is implanted within the body lumen, such that the cathode is disposed upstream of the anode.

29. The method of claim 1, wherein the implant is implanted within the body lumen, such that the uncoated portion is disposed upstream of the coated portion.

30. The method of claim 1, wherein the implant includes a cylindrical wall having an exterior surface opposite the interior surface for being placed into contact with the body lumen.

31. A method of producing an oxidizing agent in a body, the method comprising:
electrochemically converting at least one substance present in a body fluid flowing in a body lumen into an oxidizing agent by implanting a tubular implant in the body lumen, the implant being partially coated with an active metal, thereby forming a coated portion of the implant and an uncoated portion of the implant for electrochemically converting at least one substance present in a body fluid flowing the body lumen into an oxidizing agent, wherein the implant is implanted within the body lumen such that one of the uncoated portion and the coated portion is disposed upstream of the other relative to the flow of the body fluid in the body lumen, wherein the coated portion and the uncoated portion are directly exposed to the flow of body fluid.

32. The method of claim 31, wherein the electrochemically converting the at least one substance present in the body fluid into the oxidizing agent comprises direct conversion.

33. The method of claim 31, wherein the electrochemically converting the at least one substance present in the body fluid into the oxidizing agent comprises indirect conversion.

34. The method of claim 31, wherein the at least one substance is a normal body fluid constituent.

35. The method of claim 34, wherein the normal body fluid constituent is selected from the group consisting of water and molecular oxygen.

36. The method of claim 31, wherein the active metal comprises zinc.

37. The method of claim 31, wherein the active metal comprises iron.

38. The method of claim 31, wherein the implant is a stent formed of a biologically inert metal partially coated with the active metal.

39. The method of claim 38, wherein the coated portion is operative as an anode, and the uncoated portion is operative as a cathode.

40. The method of claim 39, wherein the implant is implanted with the coated portion downstream of the uncoated portion, so that the oxidizing agents produced at the cathode migrate downstream with the body fluid to effect therapy at the anode.

41. The method of claim 39, wherein the coated and uncoated portions are equally distributed along a length and a width of the stent.

42. The method of claim 31, wherein the implant is a stent formed of a biologically inert material, the stent having a piece of the active metal attached thereto.

43. The method of claim 31, wherein the coated portion is operative as an anode, and the uncoated portion is operative as a cathode.

44. The method of claim 43, wherein the implant is implanted with the portion downstream of the uncoated portion so that oxidizing agents produced at the cathode migrate downstream with the body fluid to effect therapy at the anode.

45. The method of claim 43, wherein the coated and uncoated portions are equally distributed along a length and a width of the implant.

46. The method of claim 31, wherein the implant includes a cylindrical wall having an exterior surface opposite the interior surface for being placed into contact with the body lumen.

47. A method of reducing cell proliferation in a tissue, the method comprising electrochemically converting at least one substance present in a body fluid flowing in a body lumen into an oxidizing agent by implanting a tubular implant in the body lumen, the implant being partially coated with an active metal, thereby forming a coated portion of the implant and an uncoated portion of the implant for electrochemically converting at least one substance present in a body fluid flowing in the body lumen into an oxidizing agent in an amount sufficient for reducing cell proliferation in the body lumen, wherein the implant is implanted within the body lumen such that one of the uncoated portion and the coated portion is disposed upstream of the other relative to the flow of the body fluid in the body lumen, wherein the coated portion and the uncoated portion are directly exposed to the flow of body fluid.

48. The method of claim 47, wherein the electrochemically converting the at least one substance present in the body fluid into the therapeutic agent comprises direct conversion.

49. The method of claim 47, wherein the electrochemically converting the at least one substance present in the body fluid into the oxidizing agent comprises indirect conversion.

50. The method of claim 47, wherein the at least one substance is a normal body fluid constituent.

51. The method of claim 50, wherein the normal body fluid constituent is selected from the group consisting of water, and molecular oxygen.

52. The method of claim 47, wherein the active metal comprises zinc.

53. The method of claim 47, wherein the active metal comprises iron.

54. The method of claim 47, wherein the implant is a stent formed of a biologically inert metal partially coated with the active metal.

55. The method of claim 47, wherein the implant is a stent formed of a biologically inert metal, having: a portion coated with the active metal, operative as an anode; and an uncoated portion, operative as a cathode.

56. The method of claim 55, wherein the implant is implanted with the coated portion downstream of the uncoated portion, so that the oxidizing agents, produced at the cathode migrate downstream with the body fluid to effect therapy at the anode.

57. The method of claim 55, wherein the coated and uncoated portions are equally distributed along a length and a width of the stent.

58. The method of claim 47, wherein the implant is a stent formed of a biologically inert material, the stent having a piece of the active metal attached thereto.

59. The method of claim 47, wherein the coated portion is operative as an anode, and an uncoated portion is operative as a cathode.

60. The method of claim 59, wherein the implant is implanted with the coated portion downstream of the uncoated portion, so that the oxidizing agents produced at the cathode migrate downstream with the body fluid to effect therapy at the anode.

61. The method of claim 59, wherein the coated and uncoated portions are equally distributed along a length and a width of the implant.

62. The method of claim 47, wherein the implant includes a cylindrical wall having an exterior surface opposite the interior surface for being placed into contact with the body lumen.

63. A method of producing nitric oxide in a body, the method comprising:

electrochemically converting at least one substance present in a body fluid flowing in a body lumen into nitric oxide by implanting a tubular implant in the body lumen, the implant being partially coated with an active metal, thereby forming a coated portion of the implant and an uncoated portion of the implant for electrochemically converting at least one substance present in a body fluid flowing the body lumen into the nitric oxide, wherein the implant is implanted within the body lumen such that one of the uncoated portion and the coated portion is disposed upstream of the other relative to the flow of the body fluid in the body lumen, wherein the coated portion and the uncoated portion are directly exposed to the flow of body fluid.

64. The method of claim 63, wherein the nitric oxide is operative as a vasodilating agent.

65. The method of claim 63, wherein the electrochemically converting the at least one substance present in the body fluid into the nitric oxide comprises direct conversion.

66. The method of claim 63, wherein the electrochemically converting the at least one substance present in the body fluid into the nitric oxide comprises indirect conversion.

67. The method of claim 63, wherein the at least one substance is a normal body fluid constituent.

68. The method of claim 67, wherein the normal body fluid constituent is selected from the group consisting of nitrite and nitrate ions and L-arginine.

69. The method of claim 63, wherein the at least one substance is administered to the body.

70. The method of claim 69, wherein the at least one substance is administered to the body through a diet.

71. The method of claim 69, wherein the at least one substance is administered to the body through a medical administration.

72. The method of claim 69, wherein the at least one substance is selected from the group consisting of nitrite ion, nitrate ions, and a combination thereof.

73. The method of claim 63, wherein the active metal comprises zinc.

74. The method of claim 63, wherein the active metal comprises iron.

75. The method of claim 63, wherein the implant comprises a stent formed of a biologically inert metal partially coated with the active metal.

76. The method of claim 63, wherein the implant is a stent formed of a biologically inert metal, the coated portion operative as an anode, and the uncoated portion operative as a cathode.

77. The method of claim 76, wherein the implant is implanted with the coated portion downstream of the uncoated portion, so that nitric oxide, produced at the cathode migrates downstream with the body fluid, to effect therapy at the anode.

78. The method of claim 76, wherein the coated and uncoated portions are equally distributed along a length and a width of the stent.

79. The method of claim 63, wherein the implant is a stent formed of a biologically inert material, the stent having a piece of the active metal attached thereto.

80. The method of claim 63, wherein the coated portion is operative as an anode, and the uncoated portion is operative as a cathode.

81. The method of claim 80, wherein the implant is implanted with the coated portion downstream of the uncoated portion, so that the nitric oxide produced at the cathode migrates downstream with the body fluid to effect therapy at the anode.

82. The method of claim 80, wherein the coated and uncoated portions are equally distributed along a length and a width of the implant.

83. The method of claim 63, wherein the implant includes a cylindrical wall having an exterior surface opposite the interior surface for being placed into contact with the body lumen.

* * * * *

UNITED STATES PATENT AND TRADEMARK OFFICE
CERTIFICATE OF CORRECTION

PATENT NO. : 7,727,221 B2  Page 1 of 1
APPLICATION NO. : 10/477514
DATED : June 1, 2010
INVENTOR(S) : Avi Penner et al.

It is certified that error appears in the above-identified patent and that said Letters Patent is hereby corrected as shown below:

Title Page, please insert

--(62)    Related U.S. Application Data

This application claims priority to U.S. Provisional Application Serial No. 60/300,823 filed on Jun. 27, 2001.--;

Column 1, line 4, please insert

--Related Application Data

This application claims priority to U.S. Provisional Application Serial No. 60/300,823 filed on June 27, 2001, and to PCT/IL02/00524 filed on June 2, 2002 and published as WO03/002243 on January 9, 2003. The disclosures of these applications are incorporated by reference.--.

Signed and Sealed this

Twenty-eighth Day of September, 2010

David J. Kappos
*Director of the United States Patent and Trademark Office*